(12) United States Patent
Evans et al.

(10) Patent No.: US 10,695,507 B2
(45) Date of Patent: Jun. 30, 2020

(54) NEEDLE TIP ARRANGEMENTS

(71) Applicant: Owen Mumford Limited, Oxford (GB)

(72) Inventors: Timothy Evans, Oxford (GB); Toby Cowe, Oxford (GB); Colin Webb, Oxford (GB)

(73) Assignee: Owen Mumford Limited, Oxford (GB)

( * ) Notice: Subject to any disclaimer, the term of this patent is extended or adjusted under 35 U.S.C. 154(b) by 211 days.

(21) Appl. No.: 15/501,386

(22) PCT Filed: Jul. 31, 2015

(86) PCT No.: PCT/GB2015/052223
§ 371 (c)(1),
(2) Date: Feb. 2, 2017

(87) PCT Pub. No.: WO2016/020655
PCT Pub. Date: Feb. 11, 2016

(65) Prior Publication Data
US 2017/0232208 A1    Aug. 17, 2017

(30) Foreign Application Priority Data
Aug. 6, 2014 (GB) .................................. 1413933.1

(51) Int. Cl.
*A61M 5/34* (2006.01)
*A61M 5/00* (2006.01)
(Continued)

(52) U.S. Cl.
CPC ............ *A61M 5/348* (2013.01); *A61M 5/002* (2013.01); *A61M 5/288* (2013.01);
(Continued)

(58) Field of Classification Search
CPC ........ A61M 5/348; A61M 5/343; A61M 5/34; A61M 2005/3206
See application file for complete search history.

(56) References Cited

U.S. PATENT DOCUMENTS

| | | | | |
|---|---|---|---|---|
| 1,567,463 A | * | 12/1925 | Platt ........................ | A61M 5/34 604/241 |
| 2,828,743 A | | 4/1958 | Ashkenaz et al. | |

(Continued)

FOREIGN PATENT DOCUMENTS

CN          201912564 U      8/2011

OTHER PUBLICATIONS

International Search Report and Written Opinion of the International Searching Authority issued in corresponding PCT Application No. PCT/GB2015/052223, dated Feb. 17, 2016, 16 pages.

*Primary Examiner* — Bradley J Osinski
(74) *Attorney, Agent, or Firm* — Quarles & Brady LLP (57) ABSTRACT

A needle tip (22) for being connected and disconnected in use from a needle tip support (16), comprises a needle (24) having a forward end and a rearward end and, a connector secured to the needle intermediate its ends. The connector comprises two arms (28) each extending outwardly and rearwardly relative to the needle (16) and configured to be coupled and uncoupled in use from said needle tip support, and the arms are disposed on opposite sides of the needle. Also disclosed are arrangements for storing, dispensing and later disposing such needle tips, as well as coupling interfaces between the needle tip and a needle support cap to which it is fitted in use.

32 Claims, 7 Drawing Sheets

(51) Int. Cl.
*A61M 5/32* (2006.01)
*A61M 5/28* (2006.01)

(52) U.S. Cl.
CPC ........ *A61M 5/3202* (2013.01); *A61M 5/3204* (2013.01); *A61M 5/3205* (2013.01); *A61M 5/3293* (2013.01); *A61M 5/34* (2013.01); *A61M 5/343* (2013.01); *A61M 2005/3206* (2013.01)

(56) References Cited

U.S. PATENT DOCUMENTS

| | | | |
|---|---|---|---|
| 3,294,089 A | | 12/1966 | Brookfield |
| 5,458,580 A | * | 10/1995 | Hajishoreh ............. A61M 5/24 604/110 |
| 2004/0147855 A1 | | 7/2004 | Marsden |
| 2009/0099552 A1 | * | 4/2009 | Levy .................... A61M 39/10 604/533 |
| 2012/0245564 A1 | * | 9/2012 | Tekeste ............... A61M 5/3134 604/535 |

* cited by examiner

NEEDLE TIP ARRANGEMENTS

CROSS-REFERENCE TO RELATED APPLICATIONS

This application represents the U.S. National Stage of International Application No. PCT/GB2015/052223 filed Jul. 31, 2015, which is incorporated by reference in its entirety and is based on, claims priority to, and incorporates herein by reference in its entirety, British Patent Application Serial No. GB 1413933.1, filed Feb. 6, 2014, and entitled, "Needle Tip Arrangements."

This invention relates to needle tip arrangements for use with medical injection devices and to needle tip storage and dispensing arrangements.

It has been known for many years to provide pen injection devices to allow administration of an injection. Typically the pen contains a cartridge or other container of medicament that contains several doses and is designed to receive a disposable needle tip (also known as a pen needle), and the user is instructed to use a fresh needle tip for each injection. A common form of needle tip is our Unifine® Pen Tip® product which comprises a moulded plastics hub comprising a circular end wall and a cylindrical internally threaded portion, with a central double ended needle extending forwardly and rearwardly of the end wall. Many users of these devices need to inject up to seven or so times a day and users are advised to carry ten to twelve sterile packaged needle tips with them. They also need to have some means of safely disposing of the used needle tip to avoid contamination. In the conventional type of device, the needle tip is screwed onto the front end of a cartridge holder of the injection device and then removed after the injection. Conventional needle tips are packaged in sealed conical outer containers and ten or twelve of these occupy a significant volume. Likewise the used needle tips when returned to the containers need to be carried until they can be safely disposed of in a sharps container or other suitable receptacle.

The bulk occupied by a day's worth of unused and used needle tips means that users may economize on space by taking an insufficient number of needle tips with them. This can lead to multiple use of the single use needle which can be painful and also increase the risk of contamination.

We have therefore designed a needle tip system which considerably reduces the volume of the needle tip whilst maintaining the required length of the needle, and allowing connection and disconnection from an injection device. The provision of a compact needle tip reduces the storage space required for the advised number of needle tips and likewise, means that their storage prior to disposal can be compact.

According to one aspect of this invention, there is provided a needle tip for being connected and disconnected in use from a needle tip support, said needle tip including:

a needle having a forward end and a rearward end, and a connector secured to the needle intermediate its ends and comprising two arms each extending outwardly and rearwardly relative to the needle and configured to be coupled and uncoupled in use from said needle tip support, the arms being disposed on opposite sides of the needle.

This provides a greatly flattened aspect in end view, allowing compact storage before and after use.

The connector preferably includes a plug portion through which said needle extends, and which is adapted to engage a corresponding socket in said needle tip support in use, and which merges with the inner ends of said arms. The plug and socket may be configured to prevent relative rotation. Thus the plug is conveniently of non-circular cross-section.

Preferably said arms are resilient and configured to snap around corresponding locations on said needle tip support in use, to facilitate coupling and uncoupling. Each arm may include a toothed region for engagement with said needle tip support. In preferred embodiments at the interface between the needle tip and the support, the needle tip is dynamic i.e. it expands and/or contracts during the coupling and uncoupling, whilst the support plays a passive role and does not flex or move significantly.

To provide a compact arrangement the width of each of the arms, in direction transverse to a plane containing the needle, is preferably less than 10 times the diameter of the needle, and/or is less than half the maximum span of the arms in that plane.

In another aspect there is provided a needle tip as described above, in combination with a needle tip support, the needle tip support having at least one region for cooperating with said arms to allow coupling and uncoupling of the needle tip. Preferably, the needle tip support has a tapered region may be at least one surface against which said arms may latch. Said tapered region is a solid of revolution whereby there is an angular tolerance of 360° for attachment of the needle tip to the needle tip receiver; alternatively, said tapered region may be shaped to allow connection to the needle tip at only two relative angular positions.

The invention also extends to a needle tip support for use in the combination as set out above, the support including an opening for receiving in use said needle tip with the needle extending therethrough, and at least one feature remote from said opening for being engaged by the arms of said needle tip to allow releasable coupling of the needle tip to said needle tip support.

In preferred embodiments, the coupling action of the needle tip to the support is such that it is difficult or impossible to remove the needle tip from the support manually, and use of a removal tool is required.

In one arrangement the needle tip support includes a body portion of generally frusto-conical form surrounding said opening. Alternatively, the needle tip support may include a body portion of generally rectangular transverse cross-section extending to either side of said opening. This body may be trapezoidal in side view. Conveniently said opening has a non-circular cross-section, to complement a non-circular fitting on the needle tip.

According to another aspect, this invention provides a needle tip storage and dispensing arrangement comprising a housing, a needle tip magazine having an array of needle tip holding locations each for receiving in use a needle tip as set out above, the magazine being movably mounted in said housing.

The array of needle tip holding locations may be linear, angular or other suitable form. Although the magazine may be moved manually, the arrangement preferably includes a drive for moving said needle tip magazine to present successive needle tip holding locations at a coupling station. Where said array is a linear array, said drive arrangement is preferably operable incrementally to advance said needle tip magazine linearly. To preserve sterility said needle tip magazine may include seal elements disposed intermediate each two needle tip holding locations for slideably sealing against an interior surface of said housing. For example the interior surface of said housing may be cylindrical and said seal elements may extend circumferentially around the exterior of the needle tip magazine. The seal elements may comprise a coaxial array of 'O' ring elements.

The needle tip storage and dispensing arrangement preferably includes a facility for removing and storing used needle tips after use. Thus, said needle tip magazine may be provided with at least one post-use storage recess for storing a used needle tip. For example, said needle tip magazine may include a plurality of post-use storage recesses each associated with a respective needle tip holding location. It will be appreciated that each used needle tip could instead be returned to a respective empty needle holding location.

Conveniently, each needle tip holding location defines a coupling axis along which in use a needle tip is withdrawn and each post-use storage recess defines an uncoupling axis along which a needle tip is introduced into said post-use storage recess, with respective associated needle tip holding locations and post-use storage recesses being disposed with the coupling axis and the uncoupling axis generally coplanar. This provides a compact and intuitive arrangement. The coupling axis and the uncoupling axis of an associated needle tip housing location and post-use storage recess may be generally perpendicular. The needle tip holding locations and the post-use storage recesses are conveniently respectively aligned with associated holding planes and storage planes.

The or each post-use storage recess is conveniently provided with one or more latch elements for latching in use a needle tip to allow its removal from an injection device and retention in said post-use storage recess. Thus, where said needle tip includes coupling arms extending to either side of a needle for coupling the needle tip in use to a needle tip support, said latch elements may capture the arms of the needle tip in use.

In another arrangement a storage volume may form part of or be associated with said housing and is configured to receive and store in use a used needle tip received via one of said post-use storage recesses. Thus, said storage volume may be defined between an interior surface of said housing and an opposing surface of said needle tip magazine. Alternatively, said storage volume may comprise a compartment formed in said housing.

Where the array of needle tip holding locations in said magazine is an angular array, the needle tip holding locations may be spaced about the periphery of said needle tip magazine. A drive mechanism may be operable to advance said needle tip magazine angularly.

Preferably each of said needle tip holding locations comprises a recess configured to receive a needle tip in use. Said needle magazine conveniently includes a sealing element for sealing each of said needle tip locations with a needle tip contained therein. Said sealing element may cover a plurality of said needle tip locations and be bonded to said needle tip magazine by a bond that allows said sealing element progressively to be peeled from each of said needle tip locations in turn.

Advantageously, a deflector forms part of or is associated with said housing and is disposed to cause said sealing element to peel away from said housing as said needle tip magazine is moved to present a needle tip at said coupling station.

In this arrangement the sealing element may be constrained to pass down a passage as it peels off said needle tip magazine on movement of said needle tip magazine. The sealing element may provide an indication of the number of unused needle tips remaining in the magazine. For example, said passage may be provided with an externally viewable window that is occluded by said sealing element where said needle tip magazine is moved to present a last needle tip in said magazine to said coupling station. Alternatively the strip may be coloured or carry indicia that may be read externally.

According to another aspect of this invention there is provided a needle tip system comprising:

a needle tip having a needle and including or more resilient coupling means for coupling the needle to a needle tip support, said needle tip being enclosed in a tearable wrapper, a needle tip holder for accepting a wrapped needle, and a needle tip support, said needle tip support having a recess for receiving said needle tip and being configured releasably to hold a needle tip, wherein said needle tip holder is configured in use to hold the needle tip whilst said needle tip support is brought into engagement with and coupled to said needle tip as said wrapper is displaced.

Conveniently said needle tip holder includes a movable wrapper displacement element that engages and spreads said wrapper as said needle tip support is brought into engagement with said needle tip. Said wrapper displacement element may include an opening configured to pass over and engage said wrapper to spread it as said wrapper displacement element moves relative to said needle tip. Conveniently said wrapper displacement element may be moveable against a spring bias from an initial to a spreading position. Conveniently said needle tip holder includes at least one ramp surface that cooperates with said wrapper displacement element to spread said wrapper in use.

The invention extends to a needle tip as set out above, contained in a tearable wrapper. A shield may be provided within said wrapper for shielding at least one of said needle ends. The shield may comprise an arrangement having a forward portion which initially, at least, shields the forward end of said needle and a rearward portion that supports the connector of said needle tip, the rearward portion being movable relative to the forward portion to cause a rearward portion needle of said needle tip to pierce said wrapper.

Conveniently relative separating movement of said forward and rearward portions causes said wrapper to be drawn apart when said rearward needle portion pierces said wrapper. Thus said forward and rearward portions may comprise oppositely facing wedges defining a waisted portion, whereby a manual pinching action causes said forward and rearward parts to separate and said wrapper to be placed under tension, whereby on said needle piercing said wrapper, the wrapper is drawn away from said needle tip.

According to another aspect of this invention there is provided a connection arrangement for being applied in use to a wrapper of sheet material enclosing a needle tip to allow a plurality of said wrappers to be connected together in use, said connection arrangement comprising first and second connector portions configured to be fitted together through walls of said wrapper, said first and second connector portions also defining respective complementary coupling portions that allow in use a connection arrangement to be connected to a like connection arrangement.

Whilst the invention has been described above, it extends to any inventive combination of features set out in the following description, claims or drawings.

The invention may be performed in various ways, and, by way of example only, various embodiments thereof will now be described in detail, reference being made to the accompanying drawings in which:

FIGS. 6(a), (b), (c) and (d) are side and end views on another embodiment of needle tip and needle tip support;

FIGS. 7(a), (b), (c) and (d) are side and end views on another embodiment of needle tip and needle tip support;

FIGS. 8(a) and (b) are vertical section lines taken perpendicularly through a needle tip storage and dispensing arrangement;

FIGS. 9(a) and (b) are a vertical section view taken through an embodiment of needle tip storage, dispensing and disposal arrangement and a side view of an inner magazine, respectively;

FIGS. 10(a) and (b) are section views taken on lines A-A of FIG. 9 showing the dispensing and disposal sockets arranged perpendicularly;

FIGS. 11(a), (b) and (c) are vertical section views through another embodiment of needle tip storage and dispensing arrangement shown prior to dispensing the first needle tip, after dispensing the first needle tip, and having dispensed the final needle tip respectively;

FIGS. 12(a) and (b) are vertical section and top views respectively of another embodiment of storage, dispensing and disposal arrangement with a facility for receiving used needle tips;

FIGS. 13 (a) and (b) are vertical section and top views respectively of another embodiment of storage, dispensing and disposal arrangement with a facility for receiving used needle tips;

FIGS. 17(a) and (b) are views of a further embodiment of a needle tip packaged in a wrapper;

FIGS. 18(a) and (b) are a section view through a packaging snap connector for the embodiment of FIG. 17 applied to the packaging, and a section view illustrating stacking connection of the connectors respectively, and FIGS. 19(a) and (b) are perspective and side views of another embodiment of needle tip storage, dispensing and disposal arrangement.

Referring initially to FIGS. 1 to 4, the front end of an injection device 10 containing a cartridge or syringe is provided with an externally threaded collar 12 behind which is located a pierceable seal or septum 14 of a cartridge containing the medicament to be injected. The externally threaded collar 12 is of the type designed to receive an internally threaded needle tip of conventional form such as our Unifine® product. However, the needle tip system of this embodiment is made up of a needle support cap 16 having a rear cylindrical part 16' and a forward frusto-conical part 16", with the cylindrical part 16' being internally threaded so that the support cap 16 can be screwed onto the threaded collar 12 and left there during successive changes or needle tip. The frusto-conical part 16" of the support cap 16 has a central aperture 18. Externally, at the merger between the cylindrical part and the frusto-conical part, there is provided an annular groove 20.

Figure 1:
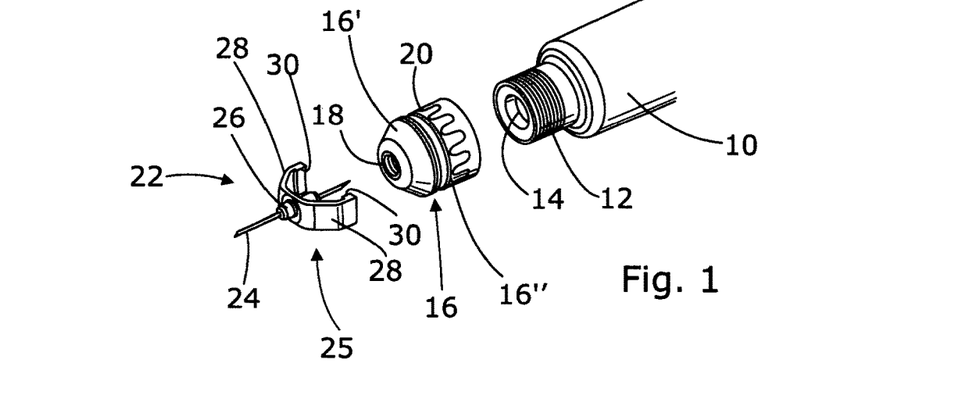
FIG. 1 is an exploded view of an embodiment of a needle tip system.

The needle tip 22 is very compact and comprises a double ended needle 24 having a rearward sharpened end for piercing the seal 14 when the needle tip is connected to the support cap 16, and a sharpened patient end. Moulded or otherwise suitably secured to a central portion of the needle is a connector 25 of slimline form comprising a boss 26 and two rearwardly and outwardly extending arms 28. At the inner ends of each of the arms is a toothed rib 30. The needle tip may be introduced and connected to the support cap 18 by passing the rear end of the needle and the rear portion of the boss 26 through the aperture 18 (piercing the seal) until the inner surfaces of the arms lie against the frusto-conical portion of the support cap and the toothed ribs 30 snap into the annular groove 20 to clasp the needle tip securely against the support cap.

The boss 26 releasably plugs into the aperture 18 to provide stability for the needle. The injection device may then be used in the usual manner. After use, the needle tip may be unclasped from the support cap by using a tool (to be described below) to lift the toothed ribs 30 out of the annular groove 20 and pulling the needle tip 22 away so that it can be disposed of safely. Due to the slimline profile of the needle tip, it allows a far greater packing density of the needle tip in a restricted space for either dispensing or safe disposal.

In preferred embodiments, the interface between the toothed ribs 30 and the annular groove 20 is designed so that the toothed ribs cannot be released by pulling the needle tip forwardly by the needle 24 or by the boss 26. The needle tip holds on to the support cap tightly by the snap action and can only be dislodged by lifting the toothed ribs out of the groove laterally. For example the contacting surfaces of the toothed ribs and the groove may be inclined at an angle greater than 90° to the needle axis so the toothed ribs are pulled into tighter engagement with the groove if an attempt is made manually to pull the needle tip forwardly off the support cap. Instead, needle tip removal requires an implement, tool or removal surface to be inserted behind the rear facing ends of the arms to lift them clear of the groove and to push the needle tip away from the support cap. This encourages compliance because users find it difficult or impossible to remove unless they use specific removal features of the type described below, which then drop the used needle tip directly into the sharps container.

Figures 2, 3:
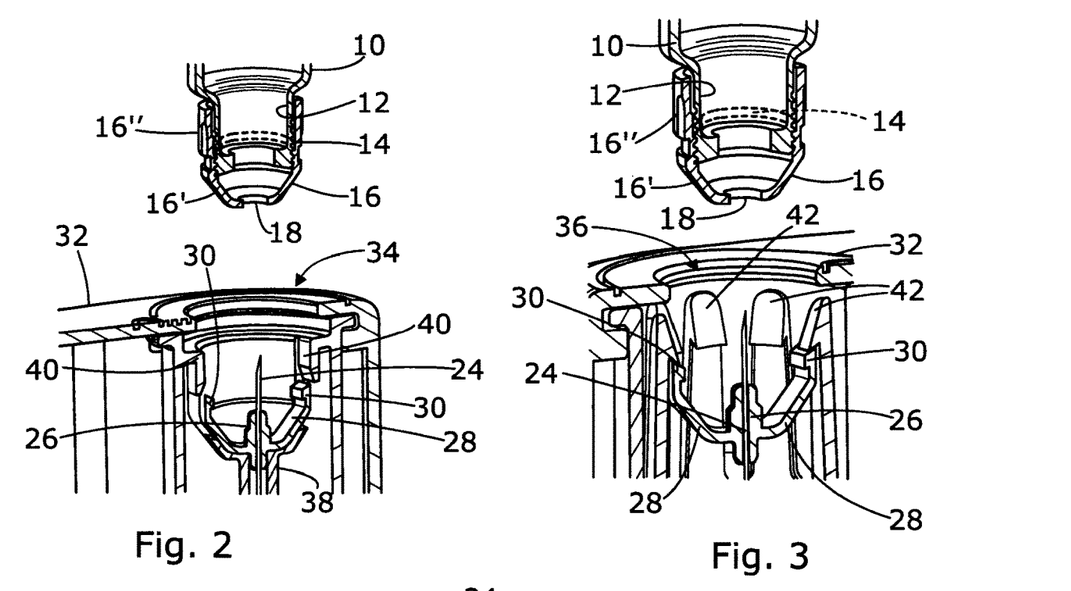
FIG. 2 is a detailed cutaway view of an embodiment of a dispensing socket.
FIG. 3 is a detailed cutaway view of an embodiment of a removal socket.
Figure 4:
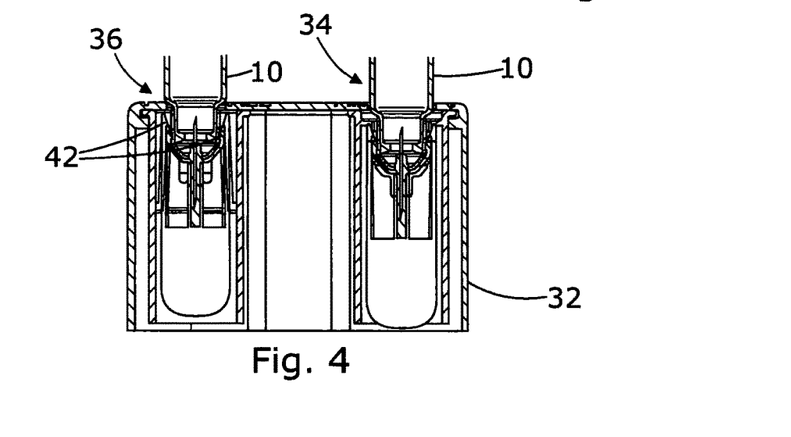
FIG. 4 is a cross-sectional view of an embodiment of a dual dispenser/disposal arrangement.

FIGS. 2 to 4 show a dispensing arrangement having an outer housing 32 defining a dispensing socket 34 and a removal/disposal socket 36. Referring to the dispensing socket 34, this allows a user to insert the support cap of an injection device into the socket and pick up a needle tip. A needle tip 22 (or a stack thereof) is supported on a cradle 38 having a central passage for receiving the forward end of the needle 24. Where the dispensing socket contains a stack of needle tips, the cradle may be sprung to advance upwardly each time a needle tip is dispensed. Within the dispensing socket 34 are two diametrically opposed lugs 40 which temporarily restrain the needle tip 22 and which also may allow the user angularly to orient the injection device with the needle tip 22 for correct coupling.

The removal/disposal socket 36 is similarly sized to the dispensing socket 34 to allow a user to insert the support cap 16 and attached needle tip 22 into the socket. The socket 36 is provided with a number of axially directed claw fingers 42 configured to snap around the rearward facing end of the arms 28 of a needle tip when inserted into the socket. In use a user may push the support cap 16 with attached needle tip 22 into the socket 36 and then remove the needle tip simply by pulling the injection device away from the outer housing 32, leaving the used needle tip trapped therein. A suitable void may be provided below the removal socket into which used needle tips may fall once detached from the injection device, with a suitable baffle or other arrangement to prevent the re-emergence thereof.

Figure 5:
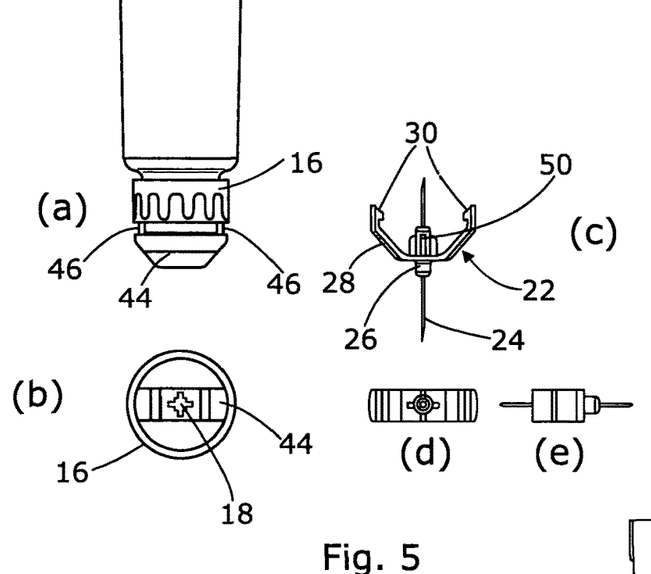
FIGS. 5(a) to (e) are side and end views on another embodiment of a needle tip and needle tip support.
Figure 6:
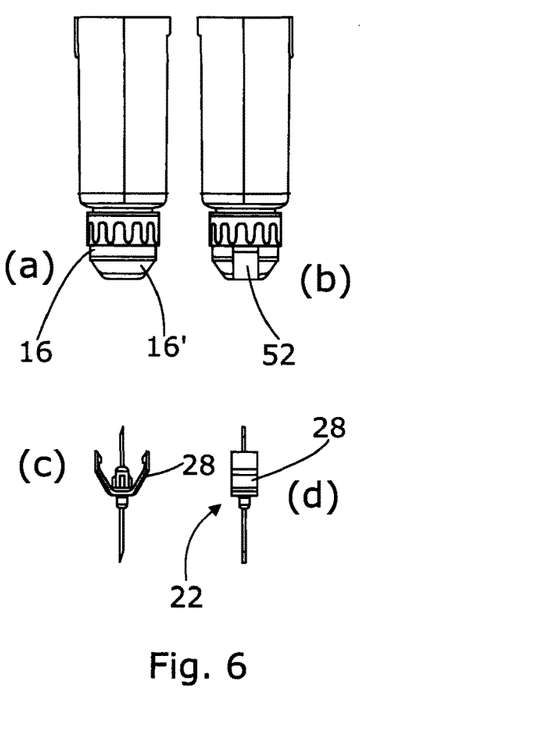
Figure 7:
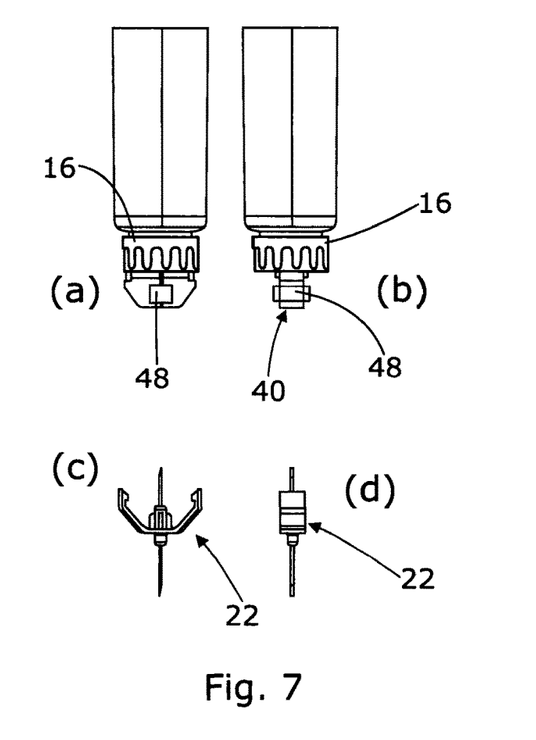

FIGS. 5 to 7 show a number of different variations of interface between a needle tip 22 and a support cap 16. In each case, the needle tip 22 is of generally the same form except in FIG. 6 where the spread of the arms 28 is not as great as the other embodiments. In the arrangement of FIGS. 5(a) and (b), there is a central trapezoidal-shaped rib 44 of substantially uniform thickness with notches 46 at opposite ends into which the toothed ribs 30 of the arms 28 of the needle tip 22 clip. In order to provide a keying feature, two lugs 48 may protrude from either side of the trapezoidal section, as shown in FIG. 7. The rearward end of the boss may carry ribs or splines 50 to provide the boss with a cruciform cross-section, and the opening 18 in the support cap 16 may be complementarily shaped to prevent the needle tip 22 from rotating and potentially uncoupling from the support cap 16. In FIGS. 6(a) and (b), the support cap 16 is of generally frusto-conical shape as in the cap of FIG. 1, but is provided with a central relieved portion 52 into which the arms 28 of the needle tip slot, so that the forward faces of the arms 28 and the frusto-conical portion $16^1$ are flush.

Referring now to FIGS. 8 to 14, there are shown various forms of needle tip dispenser for keeping the needle tips 22 in a sterile condition until they are required for use, and then presenting them for being picked up by the needle support cap 16. Thus, in the embodiment of FIGS. 8(a) and (b), an outer housing 100 slideably receives an inner magazine 110 which includes a vertical array of needle storage slots 112. The magazine is provided with a number of 'O' ring seals 114, one between each pair of storage slots 112 respectively, and one at the top and bottom, so as to preserve the sterility of the remaining needle tips 22 when one is exposed for being picked up by the needle support cap 16. An indexing mechanism 114 is provided to shift the magazine downwardly by suitable increment upon each activation to present a next needle tip. In this arrangement an elongate fir tree shaped recess 116 is provided in the magazine 110 which acts like a ratchet surface in combination with a button 118 having flexible fingers 120 at the bottom end of a stem 122. Each time the button 118 is depressed, the magazine 110 is advanced by an amount equivalent to the spacing between two needle storage slots 112, to present the next one ready for the injection device.

This arrangement can be modified to allow for needle disposal as well as needle dispensing. Thus, in FIGS. 9 and 10, the magazine 110 of is provided with a series of disposal slots 122 extending at 90° to each needle storage slot. The disposal slots 122 include latch fingers 124 past which the ends of the arms 28 of a needle tip 22 snap when a needle tip is introduced into the slot. Withdrawing the injection device then unclasps the needle tip from the needle cap support 16, leaving the needle tip 22 trapped inside the disposal slot 122.

Figure 8:
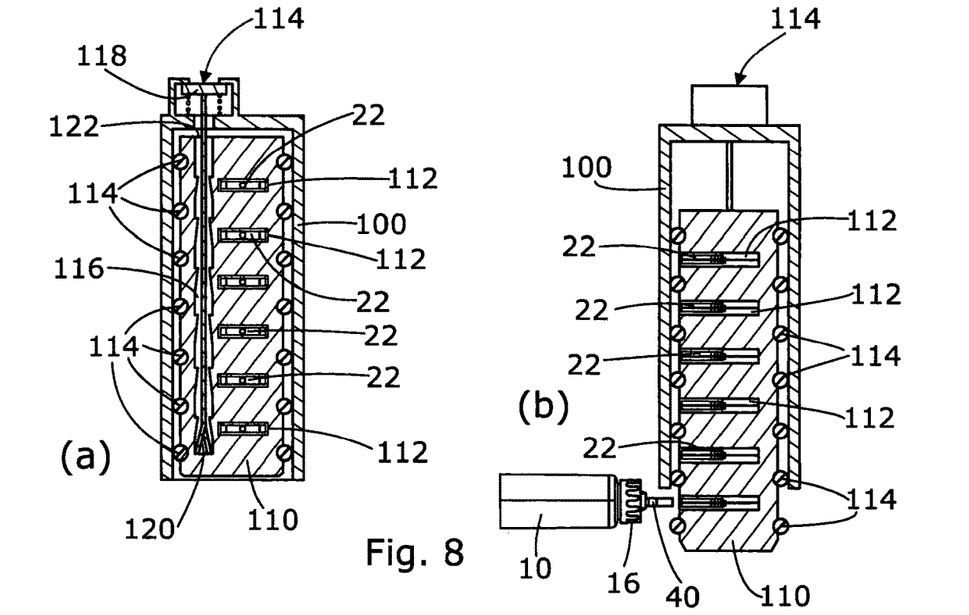
Figures 9, 10:
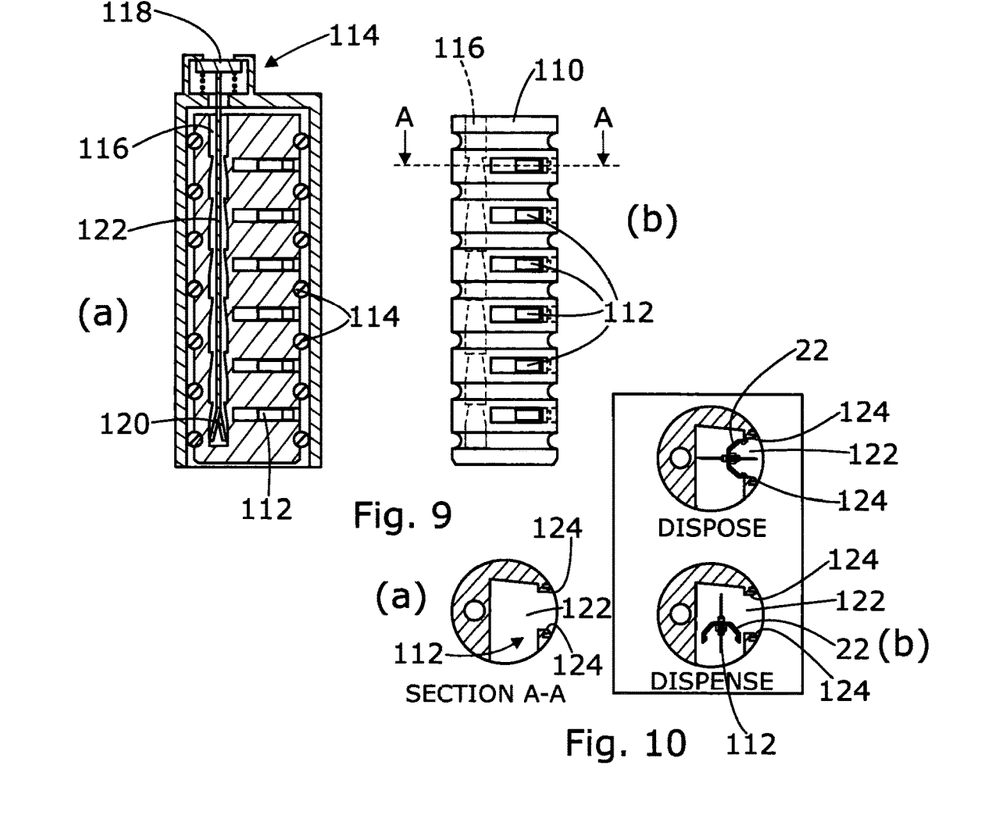
Figure 11:
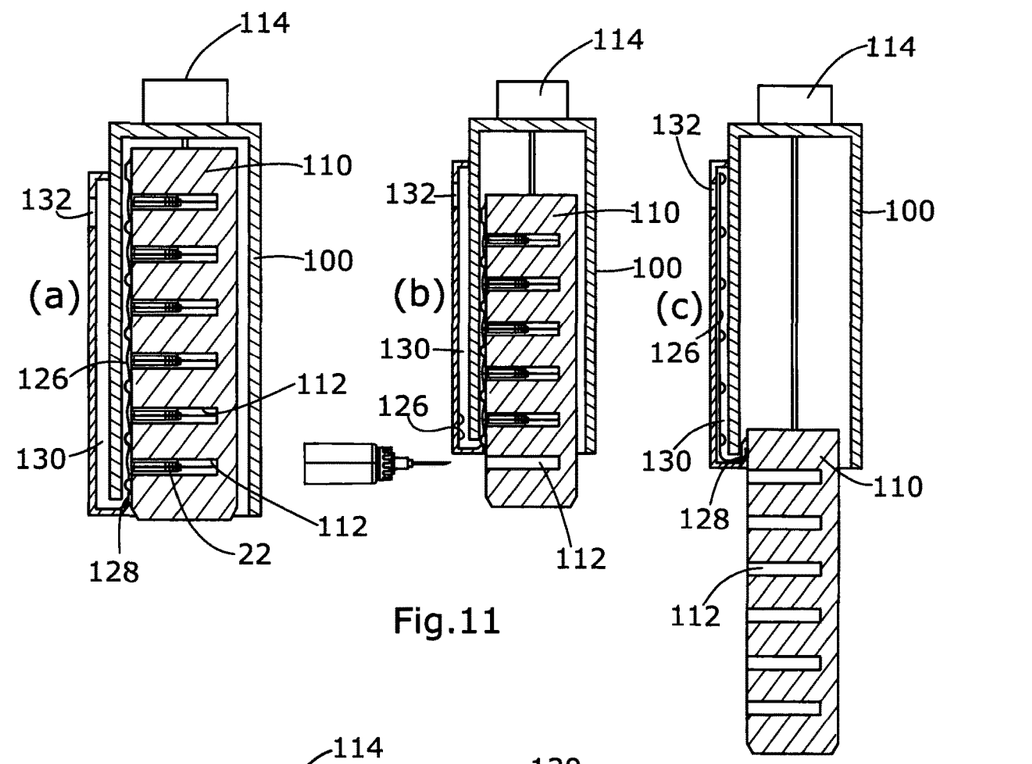
Figure 12:
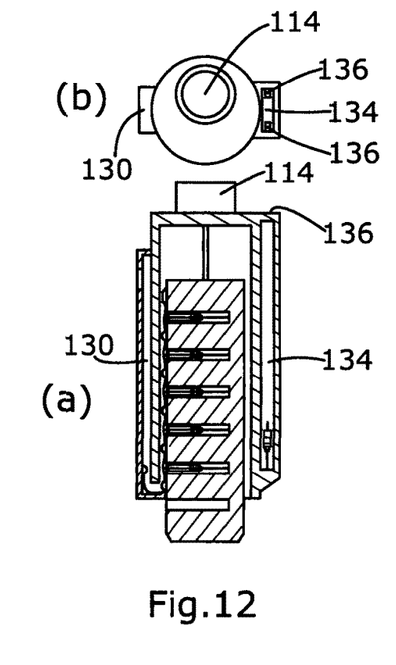
Figure 13:
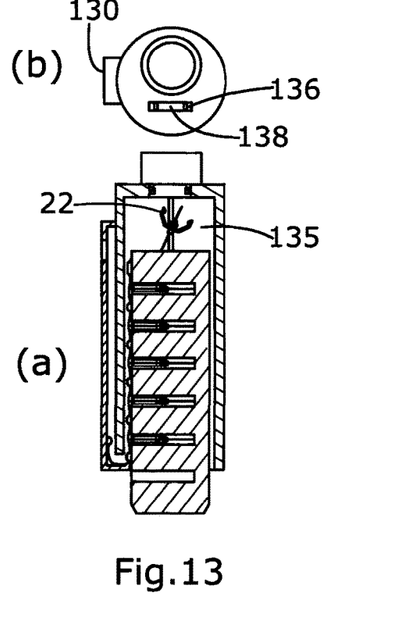

Referring now to FIG. 11, this arrangement is generally similar to that of FIG. 8 except that, instead of using spaced 'O' ring seals to preserve sterility, the needle tips are initially sealed in their storage slots by means of a suitable elongate tape 126 of paper, foil, etc. As before, the magazine is indexed down to present successive needle slots 110 ready to allow the injection device to pick up a next needle tip. The housing is provided with a scoop edge and deflection arrangement 128 which, as the magazine is indexed down, peels the foil tape away from the magazine to reveal the next slot 112, with the peeled foil passing into an elongate slot 130 in the housing. At its upper end, the elongate slot 130 has a window 132, and the slot 130 and the window 132 are designed with reference to the length of the foil tape 126 such that the end of the foil tape becomes visible in the window 132 as the magazine is indexed to present the last available needle slot. This provides the user with a warning when the last tip has been dispersed.

The arrangement of FIG. 11 may be modified to allow removal and disposal of used needle tips. Thus, in FIGS. 12(a) and (b), a separate needle removal compartment 134 is provided on a side of the housing opposite the elongate slot 130. The removal compartment includes an aperture at its upper end with latch arms 136 designed to snap around the arms 28 of the needle tip 22 when presented in the aperture, with the needle tip separating from the injection device as it is pulled away from the dispenser, the needle tip 22 then falling down into the base of the removal compartment 134 as shown. Instead of providing a separate removal compartment 134, use may be made of the expanding void 135 that is defined between the upper end of the magazine 110 and the housing 100 as the magazine 110 is indexed downwardly to present each new needle tip. Thus, in FIGS. 13(a) and (b), the upper end of the housing is provided with a removal slot 138 with latch arms 136 similar to those of FIG. 11. A user may offer up the injection device so that the needle tip 22 is captured and removed and then subsequently drops into the void 135 between the magazine and the housing after separation.

Figure 14:
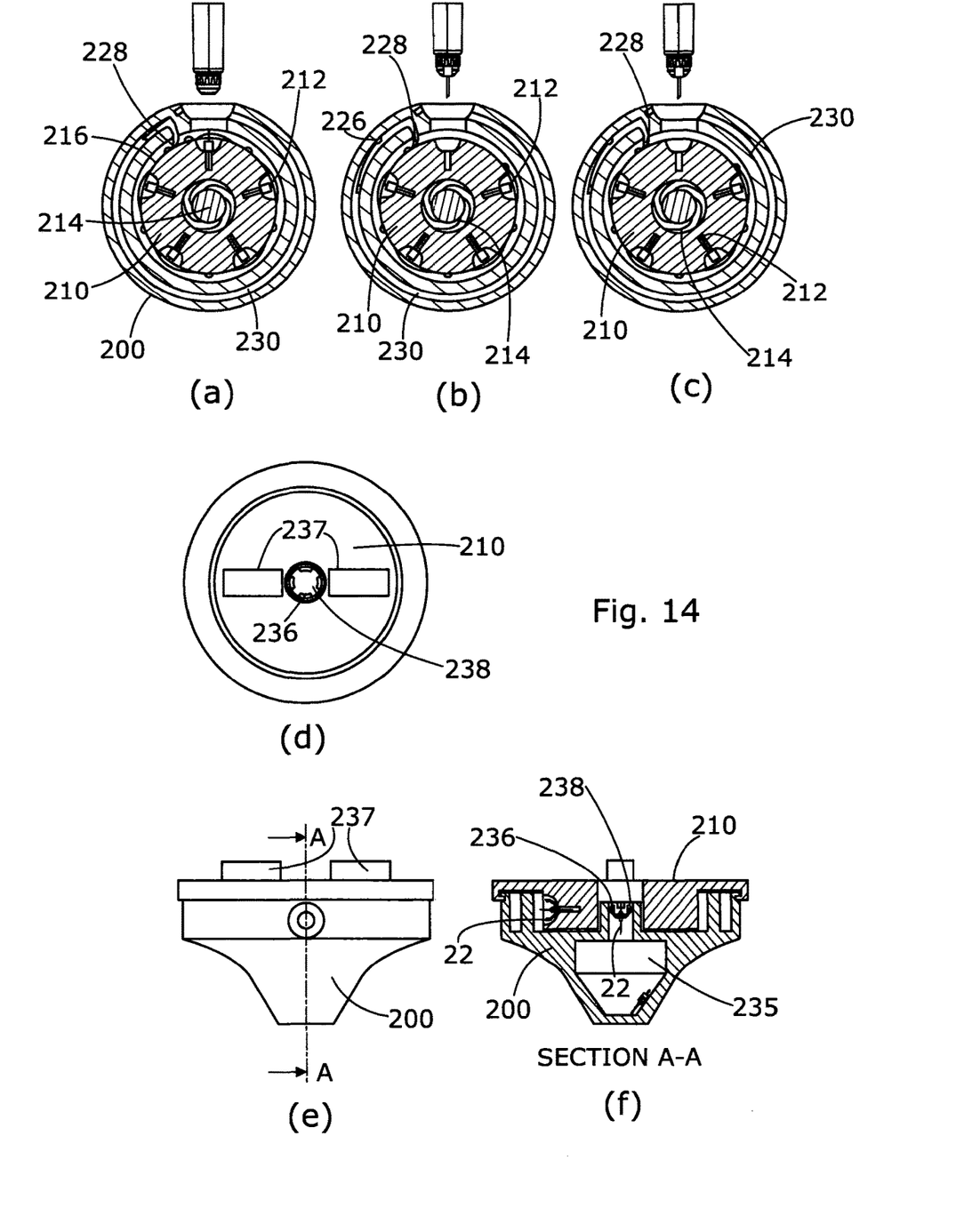
FIGS. 14(a) to (f) are three horizontal section views taken through a rotary version of a needle tip storage, dispensing and disposal arrangement shown before dispensing the first needle tip, after dispensing the first needle tip, and having dispensed the final needle tip respectively, and top, side and vertical section views.

Referring now to FIG. 14, the arrangement of FIG. 8 may be configured to be angularly indexed as opposed to linearly indexed. Thus, in this arrangement there is a central disk shaped magazine 210 with regularly extending needle tip slots 212 covered initially by a suitable foil 226 or other seal. The magazine is contained for rotation within an outer housing 200 which is provided with an annular passage 230 for receiving the seal as it is peeled off the surface of the magazine. The housing includes scoop surface 228 to achieve this. The magazine rotates around a central shaft and a ratchet 214 arrangement is provided to constrain rotation in one direction only, and upstanding tabs 237 are provided to allow manual rotation. As seen in FIG. 14(c), the housing may be provided with a central void 235 communicating with a central removal aperture 238 having removal latches 236 designed to capture a needle tip 22 when it is offered up to the aperture.

It will be appreciated that the interfaces between the needle support cap and the needle dispensing and optional removal arrangements may take any of the forms shown in FIG. 1 or 5 to 7.

Figure 15:
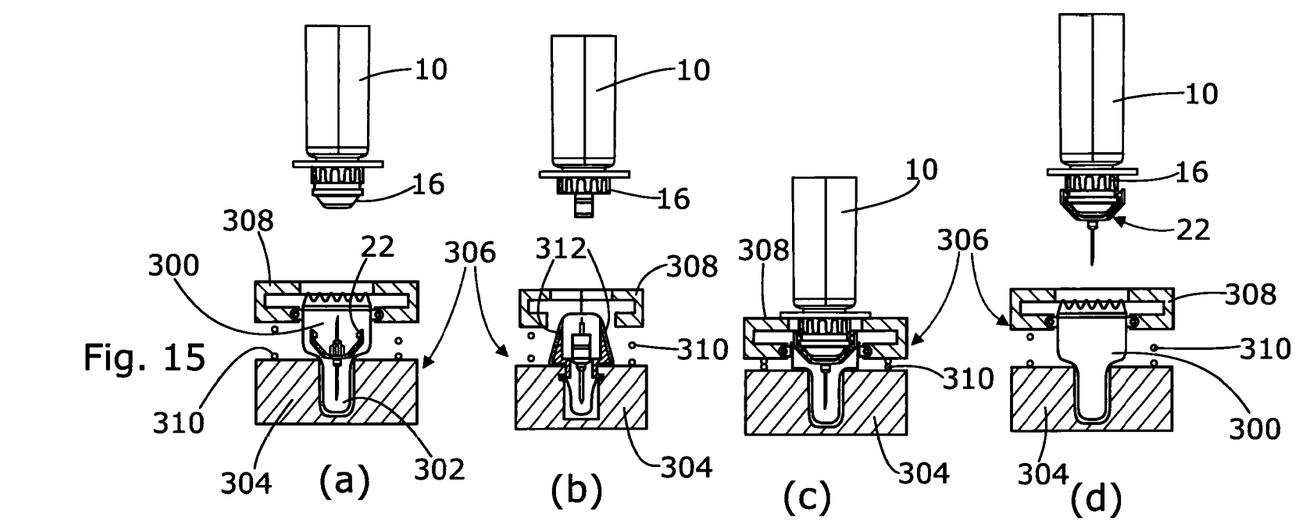
FIGS. 15(a) to (d) are section views through an embodiment of an arrangement for docking and connecting a needle tip support with a pre-wrapped needle tip.

Referring now to FIG. 15, the needle tip 22 of the type described above may be presented in the form of individual, heat-sealed packets 300 to maintain sterility and which must be opened to allow access to the needle, prior to fitting the needle tip to the injection device. In the arrangement of FIG. 15, a needle tip 22 in a heat-sealed sleeve 300 is located in the well 302 of the base 304 of an applicator device 306. The applicator device comprises the base 304 and an apertured plunger 308 that is biased by a spring 310 to a rest position at a distance from the base. The base also includes two upstanding ramps 312 positioned to either side of the well (see FIG. 15(b)). In use, an injection device 10 is applied to the upper end of the plunger 308 with the cap 16 in the aperture of plunger 308, and then the injection device and the plunger 308 together pushed downwardly. This has the effect of trapping parts of the wrapper sleeve 300 between the ramp and the aperture of the plunger 38 so that the wrapper is first drawn tightly against the non-patient end of the needle 24 to puncture the wrapper, and then drawn away from the needle as the plunger draws spaced portions of the wrapper down the ramp. At the bottom of the stroke of the plunger, the needle support cap 16 snaps into engagement with the needle tip 22 so that when the injection device is pulled clear of the applicator, it carries the needle tip, leaving the wrapper 300 behind.

Figure 16:
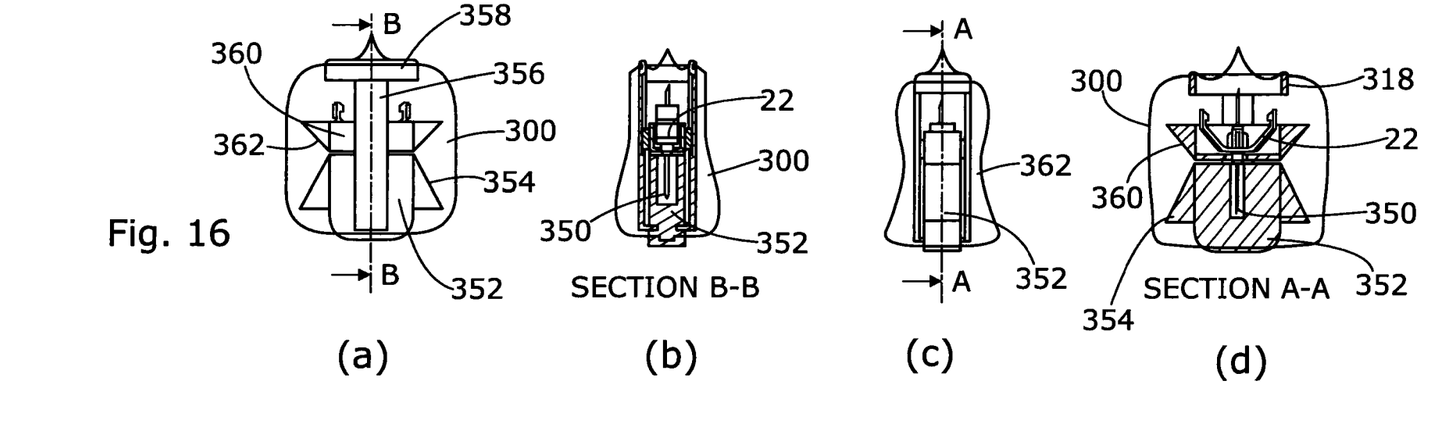
FIGS. 16(a) to (d) are front and side views and corresponding section views of an embodiment of a needle tip packaged in a wrapper.

Instead of providing an external mechanism or adapter to spread the wrapper away from the needle once it has been punctured thereby, an internal mechanism may be provided within the wrapper that achieves this function and also provides initial protection for the exposed needle portions. In FIG. 16, the needle tip 22 is initially provided with its forward needle portion located in a bore 350 in a lower protector component 352. The lower protector component 352 has a tapered skirt 354 and opposed legs 356 extend rearwardly to carry a protection ring 358 at their upper ends. An upper protector component 360 also with a tapered skirt 362 is arranged opposite the lower component 352 to provide a waisted portion, and receives the arms 28 of the needle tip 22 and is slideably mounted on the legs 356 of the lower component. This combination, including the needle tip, is located inside the outer sleeve 300. When a user wishes to prepare the package to allow the needle tip to be connected to an injection device, they pinch the protection component about its waist. This action causes the two components to separate, and the needle tip 22 and the non-patient end of the needle tip move upwardly with the upper component 360 to pierce the wrapper 300. At the same time, the effective elongation of the protection component causes the wrapper 362 to be drawn tightly across the ring 358 as it is pierced by the needle so that it is drawn clear to allow the needle tip to be picked up cleanly by the injection device.

Figure 17:
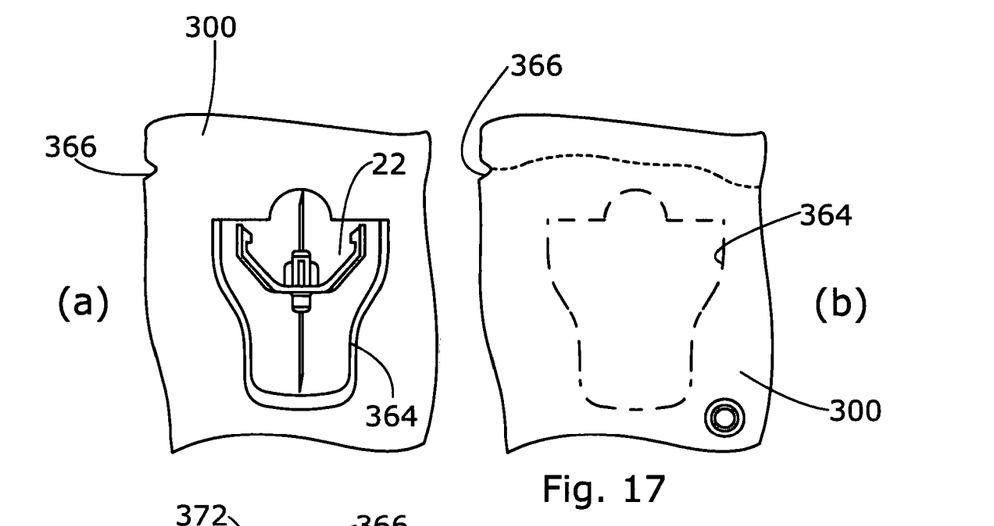

In another arrangement illustrated in FIG. 17, the needle tip is provided in a heat-sealed wrapper 300 with just a rigid shroud 364 to prevent damage to the needle before use. The packet may have a simple tear notch 366 to allow access to the needle tip 22. Here the user may simply rip the package at the tear notch to open the packet, and then introduce an injection device to access and clip on to the needle tip.

Figure 18:
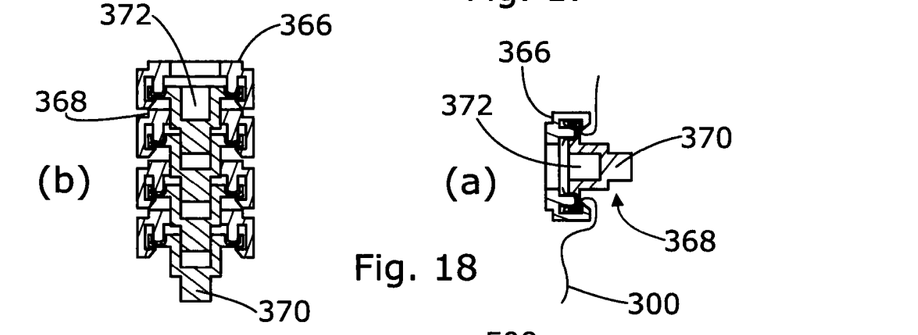

In order to allow several of the packets as shown in FIG. 17 to be connected together without compromising the sterility of the package, they may employ the two part clip ring that is illustrated in FIG. 18(a). The ring comprises two complementary parts 366, 368 and which can be located to either side of the opposed walls of a wrapper sleeve 300 and then pushed together to clip non-releasably to each other. The two part component, once assembled, provides a male plug 370 that can clip into a female socket 372 of an adjacent component, as seen in FIG. 18(b), so that a stack of wrapped needle tips may be assembled.

Figure 19:
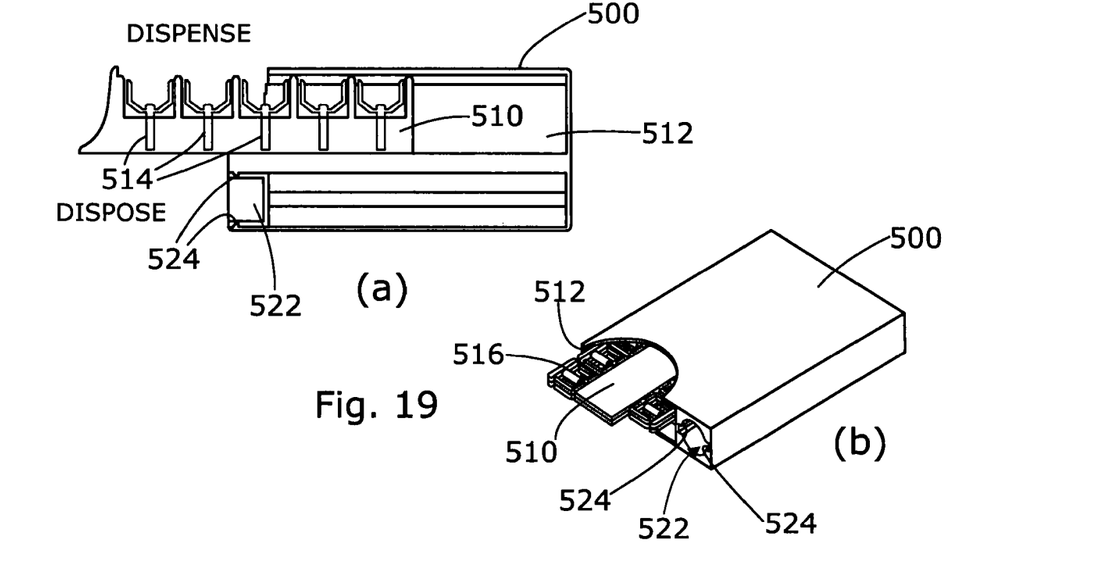

In another embodiment, illustrated in FIGS. 19(a) and (b), a magazine 510 of needle tips is of flat rectangular form and slideably received in a drawer slot 512 of a housing 500. The forward ends of the needle tips are received in bores 514 in the magazine, and the rearward ends may carry shields 516. A removal compartment and socket 522 with latches 524 to capture a used tip is provided alongside the drawer slot and is sized to receive the needle tips as they are removed by the latches 524. The recess may include guide grooves in opposite walls to align used needle tips.

The invention claimed is:

1. A needle tip for being connected and disconnected in use from a needle tip support, said needle tip including
   a needle having a forward end and a rearward end, and
   a connector secured to the needle intermediate the forward and rearward ends of the needle and comprising two arms each extending outwardly and rearwardly relative to the needle and configured to be coupled and uncoupled in use from said needle tip support, the arms being disposed on opposite sides of the needle,
   wherein the connector includes a plug portion through which the needle extends, and which includes a portion of non-circular cross-section extending rearwardly along the needle from inner ends of the arms for engaging a complementary socket in the needle tip support in use to prevent relative rotation therebetween, and which merges with the inner ends of the arms,
   wherein a diameter of the plug portion is equal to or less than a width of the arms, and
   wherein an end of each of the arms is adapted to interact with a latch of a needle tip removal device.

2. A needle tip according to claim 1 wherein said arms are resilient and configured to snap around corresponding locations on said needle tip support in use, to allow coupling and uncoupling.

3. A needle tip according to claim 1, in combination with a needle tip support, the needle tip support having at least one region for cooperating with said arms to allow coupling and uncoupling of the needle tip.

4. A combination according to claim 3, wherein the needle tip support has a tapered region having at least one surface against which said arms may latch.

5. The combination according to claim 4, wherein said tapered region is a solid of revolution.

6. The needle tip support for use in the combination according to claim 3, which includes an opening for receiving in use the plug portion of the needle tip with the needle extending therethrough, and at least one feature remote from said opening for being engaged by the arms of said needle tip to allow releasable coupling of the needle tip to said needle tip support,
   wherein the opening has a non-circular cross-section to complement the non-circular cross-section of the plug portion.

7. The needle tip support according to claim 6, which includes a body portion of generally frusto-conical form surrounding said opening.

8. The needle tip support according to claim 6, which includes a body portion of generally rectangular transverse cross-section extending to either side of said opening.

9. The needle tip support according to claim 6, wherein the at least one feature remote from said opening comprises an annular retention groove.

10. The combination according to claim 3, wherein the at least one region of the needle tip support comprises an annular retention groove.

11. The combination of claim 3, wherein the needle tip support further includes a rear cylindrical portion which is internally threaded for engaging a syringe having complementary external threading.

12. The needle tip according to claim 1, wherein each arm includes a toothed region for engagement with said needle tip support.

13. The needle tip according to claim 1, wherein the width of each of the arms, in a direction transverse to a plane containing the needle, is less than 10 times the diameter of the needle.

14. The needle tip according to claim 1, wherein the width of each of the arms in a direction transverse to a plane containing the needle is less than half the maximum span of the arms in that plane.

15. A needle tip according to claim 1, contained in a tearable wrapper.

16. The needle tip in a wrapper according to claim 15, which further includes a shield within said wrapper for shielding at least one of said needle ends.

17. The needle tip in a wrapper according to claim 16, including a shield arrangement having a forward portion which initially, at least, shields the forward end of said needle and a rearward portion that supports the connector of said needle tip, the rearward portion being movable relative to the forward portion to cause a rearward portion of the needle of said needle tip to pierce said wrapper.

18. A needle tip in a wrapper according to claim 17, wherein relative separating movement of said forward and rearward portions causes said wrapper to be drawn apart when said rearward needle portion pierces said wrapper.

19. A needle tip in a wrapper according to claim 18, wherein said forward and rearward portions comprise oppositely facing wedges defining a waisted portion, whereby a manual pinching action causes said forward and rearward portions to separate and said wrapper to be placed under tension, whereby on said needle piercing said wrapper, the wrapper is drawn away from said needle tip.

20. The needle tip of claim 1, wherein the arms extend rearwardly in a shape complementing a frusto-conical shape of the needle tip support.

21. The needle tip of claim 20, wherein each of the arms comprises:
a first portion associated with the plug portion and extending perpendicular to a long axis of the needle,
a second portion connected to the first portion and angled rearward, and
a third portion connected to the second portion and extending rearward parallel to the long axis of the needle.

22. The needle tip of claim 21, wherein the third portion of each of the arms comprises a toothed rib on an inner side thereof for engaging with the needle tip support.

23. The needle tip of claim 1, wherein the width of the arms is greater than a thickness of the arms.

24. The needle tip of claim 1, wherein the width of the arms is measured perpendicular to a long axis of the needle and perpendicular to the outward extent of the arms.

25. A needle tip and a needle tip support, the needle tip being connected and disconnected in use from the needle tip support,
the needle tip including:
a needle having a forward end and a rearward end, and
a connector secured to the needle intermediate the forward and rearward ends of the needle and comprising two arms each extending outwardly and rearwardly relative to the needle and configured to be coupled and uncoupled in use from the needle tip support, the arms being disposed on opposite sides of the needle and an end of each of the arms being adapted to interact with a latch of a needle tip removal device,
the connector including:
a plug portion through which the needle extends, and
a portion of non-circular cross-section extending rearwardly along the needle from inner ends of the arms for engaging a complementary socket in the needle tip support to prevent relative rotation therebetween,
the plug portion merging with the inner ends of the arms; and
the needle tip support including:
an annular retention groove for cooperating with the arms to allow coupling and uncoupling of the needle tip, and
an opening having a non-circular cross-section which provides the complementary socket for the portion of the connector having the non-circular cross-section.

26. The needle tip and needle tip support of claim 25, wherein the needle tip support has a frusto-conical shape.

27. The needle tip and needle tip support of claim 26, wherein the arms extend rearwardly in a shape complementing the frusto-conical shape of the needle tip support.

28. The needle tip and needle tip support of claim 27, wherein each of the arms comprises:
a first portion associated with the plug portion and extending perpendicular to a long axis of the needle,
a second portion connected to the first portion and angled rearward, and
a third portion connected to the second portion and extending rearward parallel to the long axis of the needle.

29. The needle tip and needle tip support of claim 28, wherein a width of the arms is greater than a thickness of the arms.

30. The needle tip and needle tip support of claim 29, wherein the width of the arms is measured perpendicular to a long axis of the needle and perpendicular to the outward extent of the arms.

31. The needle tip and needle tip support of claim 28, wherein the third portion of each of the arms comprises a toothed rib on an inner side thereof for engaging with the annular retention groove of the needle tip support.

32. The needle tip and needle tip support of claim 25, wherein the needle tip support further includes a rear cylindrical portion which is internally threaded for engaging a syringe having complementary external threading.

* * * * *